United States Patent
Dunet et al.

(10) Patent No.: US 9,908,061 B2
(45) Date of Patent: Mar. 6, 2018

(54) METHOD FOR RECOVERING LOW-TEMPERATURE HEAT AND APPLICATION OF THE METHOD TO AN AROMATICS COMPLEX

(71) Applicant: AXENS, Rueil Malmaison (FR)

(72) Inventors: Alain Dunet, Massy (FR); Isabelle Prevost, Rueil Malmaison (FR); Thierry Leflour, Paris (FR)

(73) Assignee: AXENS, Rueil Malmaison (FR)

( * ) Notice: Subject to any disclaimer, the term of this patent is extended or adjusted under 35 U.S.C. 154(b) by 355 days.

(21) Appl. No.: 14/646,434

(22) PCT Filed: Oct. 17, 2013

(86) PCT No.: PCT/FR2013/052481
§ 371 (c)(1),
(2) Date: May 21, 2015

(87) PCT Pub. No.: WO2014/080102
PCT Pub. Date: May 30, 2014

(65) Prior Publication Data
US 2015/0336023 A1    Nov. 26, 2015

(30) Foreign Application Priority Data
Nov. 22, 2012 (FR) ...................... 12 03145

(51) Int. Cl.
*B01D 3/14* (2006.01)
*B01D 1/28* (2006.01)
(Continued)

(52) U.S. Cl.
CPC ............... *B01D 3/146* (2013.01); *B01D 1/28* (2013.01); *B01D 1/2856* (2013.01); *B01D 3/007* (2013.01);
(Continued)

(58) Field of Classification Search
CPC ....... B01D 3/007; B01D 3/146; B01D 3/2856
See application file for complete search history.

(56) References Cited

U.S. PATENT DOCUMENTS 3,243,359 A * 3/1966 Schmidt ................. B01D 1/007
159/17.2
4,566,947 A    1/1986 Tsuruta
(Continued)

FOREIGN PATENT DOCUMENTS

| | | |
|---|---|---|
| DE | 19903781 A1 | 8/2000 |
| EP | 0401631 A2 | 12/1990 |
| GB | 776154 A | 6/1957 |

OTHER PUBLICATIONS

International Search Report dated Mar. 21, 2014 issued in corresponding PCT/FR2013/052481 application (pp. 1-3).

*Primary Examiner* — Jonathan Miller
(74) *Attorney, Agent, or Firm* — Millen, White, Zelano and Branigan, P.C.

(57) ABSTRACT

A method for recovering heat available at low temperature in a process and its use in order to reduce the energy consumption of the said process, and application of this method to an aromatics complex in which the low-temperature heat is recovered at the head of distillation columns in the form of low-pressure steam and is reused to reboil other distillation columns in which the operating pressure has possibly been lowered.

6 Claims, 4 Drawing Sheets

(51) Int. Cl.
*B01D 3/00* (2006.01)
*C10G 25/00* (2006.01)
*C10G 45/58* (2006.01)

(52) U.S. Cl.
CPC ............ *C10G 25/00* (2013.01); *C10G 45/58* (2013.01); *Y02P 70/34* (2015.11)

(56) References Cited

U.S. PATENT DOCUMENTS

| | | | | |
|---|---|---|---|---|
| 4,615,769 | A * | 10/1986 | Horigome | C07C 7/04 202/182 |
| 4,783,242 | A | 11/1988 | Robbins | |
| 4,992,143 | A | 2/1991 | Steude et al. | |
| 5,124,004 | A * | 6/1992 | Grethlein | B01D 1/2856 202/154 |
| 5,386,075 | A * | 1/1995 | Keil | B01D 1/2856 203/2 |
| 6,589,395 | B1 | 7/2003 | Meili | |
| 7,981,256 | B2 * | 7/2011 | Wegerer | B01D 3/14 202/153 |
| 8,609,922 | B2 * | 12/2013 | Werba | B01D 3/007 203/25 |
| 8,916,740 | B2 * | 12/2014 | Werba | B01D 3/007 203/25 |
| 8,993,825 | B2 * | 3/2015 | Werba | C07C 7/12 203/25 |
| 2004/0099521 | A1 * | 5/2004 | Demers | B01D 1/0035 203/1 |
| 2008/0190110 | A1 * | 8/2008 | Chino | F01K 17/005 60/670 |

* cited by examiner

METHOD FOR RECOVERING LOW-TEMPERATURE HEAT AND APPLICATION OF THE METHOD TO AN AROMATICS COMPLEX

FIELD OF THE INVENTION

The invention relates to the field of refining and petrochemical processes making use of at least one fractionation column and generating low-pressure steam.

The invention is applied in particular to the case of an aromatics complex that employs a large number of distillation columns. The principle of the invention is based on the generation of low-pressure (LP) steam in certain columns, the LP steam thereby generated being used as a heat-transporting fluid, with or without intermediate compression, in order for example to reboil other columns that have possibly undergone a reduction in pressure enabling the reboiler of the said columns to function at a lower temperature.

The generated LP steam may also, with or without intermediate compression, be used in order to preheat other fluids whose temperature is lower than that of the generated steam.

More generally, the operating conditions and/or the configuration of the process are modified so as to reduce on the one hand its consumption of high temperature heat in favour on the other hand of its consumption of low temperature heat (this low temperature heat being able to be produced in the complex).

The use of the LP steam that is thereby generated, combined with the modification of the operating conditions of some columns, provides a substantial overall gain in energy for an aromatics complex in terms of the consumption of fuel and electricity.

These gains are quite significant in the context of reducing energy costs and can be applied to different processes, in particular to aromatics complexes.

The present invention specifies the means enabling the heat regarded as lost on account of its low temperature (around 100° to 180° C.) to be recovered, by generating low-pressure steam that may depending on the uses possibly be recompressed in order to be used as heat transporting fluid in the reboilers of some columns and/or the pre-heaters of some processed fluids.

DISCUSSION OF THE PRIOR ART

The improvement of the energy efficiency of processes is a fundamental trend in the current economic climate. Until recently the heat available in some exchangers, and particularly in cooling towers, at a temperature in the range from 100° C. to 180° C. was regarded as lost. In fact, heat at this temperature level was not used via direct exchange with a "cold" process fluid derived from a refining or petrochemical process, for example an aromatics complex. It is known to the person skilled in the art to raise the temperature of these increasingly important amounts of heat by modifying the operating conditions of the process and/or by making the process flow scheme itself more complex.

For example, in the case of a fractionating unit such as a distillation column, the person skilled in the art knows that it is possible to increase the pressure of the distillation column, the overhead (light end) vapours then being obtained at a high temperature. However, this increase in operating pressure is inevitably accompanied by an increase in the amount of heat required for the reboiler, which then operates at a higher temperature.

BRIEF DESCRIPTION OF THE INVENTION

The present invention may be defined as a method for recovering the low temperature heat contained in some heat exchangers of a refining or petrochemical process hereinafter termed "complex".

The method forming the object of the invention consists essentially in creating a low pressure (LP) steam network generated from certain heat sources, recompressing (completely or partially) this low pressure steam in order to convert it into medium pressure (MP) steam, and using the thereby generated steams (LP and MP) as a heat source for various functions of the process. In particular the generated LP and MP steams can be used in order to provide the heat required to the reboiler of a certain number of distillation columns, after having possibly lowered the operating pressure of the said columns, so as to reduce the operating temperature of their reboilers.

In the context of the present invention low pressure (LP) steam is steam having a pressure ranging from 1 to 7 bars absolute. Medium pressure (MP) steam is defined as steam having a pressure ranging from 7 bars absolute to a value between 15 and 17 bars absolute, and high pressure (HP) steam is defined as steam having a pressure above 17 bars absolute. More specifically, the method according to the present invention may be defined as a method for recovering low temperature heat, i.e. between 100° C. and 180° C., in a refining or petrochemical process called a "complex" and comprising at least one distillation column, the said method consisting in the following steps:

1) Generation of low pressure steam (i.e. at a pressure between 1 bar absolute and 7 bars absolute (abs) (1 bar=0.1 MPa) by exchange with at least one low-temperature heat source,
2) Increasing the pressure of the generated steam in at least one compression stage, in order to generate MP stream,
3) Modification of the operating conditions and/or the configuration of the process so as to reduce on the one hand the consumption of high temperature heat in favour on the other hand of the consumption of low temperature heat, 4) Use of at least a part of the LP steam obtained from stage 1 and MP steam obtained from stage 2 in order to supply the necessary heat to the low-temperature heat consumption units obtained from stage 3.

According to one variant of the present invention, the other part of the steam obtained from stage 1 is used to generate electricity.

According to one variant of the present invention, stage 2 is carried out by means of a two-stage compressor.

According to another variant of the present invention, stage 2 is carried out by means of an ejector using the HP steam as motive fluid.

Stage 3 may be carried out in various ways that are not mutually exclusive, i.e. any combination of the various ways of implementing stage 3 remain within the scope of the present invention.

In a first embodiment stage 3 is carried out by reducing the operating pressure in one or more distillation columns of the process so as to lower the temperature of their reboiler to below the temperature of the steam obtained from stage 2.

In a second embodiment stage 3 is carried out by means of a modification of the exchanger network for pre-heating the feedstocks of the distillation columns of the complex.

According to the method of the present invention, at least some of the low-temperature heat sources enabling the low pressure (LP) steam to be generated are chosen from the condensers of some distillation columns of the complex forming a first set E1.

According to a variant of the present invention the low pressure steam obtained from stage 1 is used directly as heat transporting fluid supplied to the reboilers of some columns of the complex.

According to another variant of the present invention the low pressure steam obtained from stage 1 is used after recompression as heat transporting fluid supplied to the reboilers of some columns of the complex.

The columns in which the reboilers use directly or after compression the low pressure steam obtained from stage 1 form a second set E2 that is different from E1. A different set denotes in the context of the present invention that E1 and E2 do not have a column in common.

According to another variant, which is compatible with the two previous variants, the low pressure steam obtained from stage 1 or from stage 2 is used as heat transporting fluid in order to supply heat to the process fluids in heat exchangers.

According to another variant, which is also compatible with the previous ones, the low pressure steam obtained from stage 1 or from stage 2 is used as heat transporting fluid to supply heat to the combustion air of the furnaces in the air pre-heaters.

Finally, according to a variant of the method of the present invention some distillation columns of the set E2 function at a lower operating pressure so as to reduce the temperature required for their reboiling.

The present invention may be applied to all types of processes having low-temperature heat sources capable of generating low-pressure steam.

In particular, the present invention is applied to the so-called "aromatics complex" process that makes use of at least one extractive distillation unit (P1), a paraxylene adsorption unit (P2), a xylenes isomerisation unit (P3) and a transalkylation unit (P4), the effluents from the said units being separated in the distillation columns denoted C1 to C11 having the following meanings:

C1 reformate column, C2 xylenes column, C3 heavy aromatics column, C4 raffinate column, C5 extract column, C6 purification column, C7 deheptaniser, C8 stripper, C9 benzene column, C10 toluene column, C11 stabilisation column, aromatics complex in which:

the low temperature heat sources that are chosen in the set E1 formed by the following distillation columns C3, C4 and C5 that enable low pressure (LP) steam to be generated, the columns in which the pressure is released and to which the heat is supplied in the form of medium pressure (MP) steam after compression of the LP steam generated by the set E1 (or any one of its sub-sets), which are chosen from the set formed by the following columns C7, C8, C10, C11, the columns to which is supplied the heat of the low pressure steam generated by the set E1 (or by any one of its sub-sets), without pressure reduction. In the case of an application to the aromatics complex, this is the column C9.

In the case of the application to the aromatics complex, the set E2 of the columns using the steam generated by the columns E1 thus consists of the columns C7, C8, C9, C10 and C11.

DETAILED DESCRIPTION OF THE INVENTION

In the following description the term "process" or "complex" is used to denote any refining or petrochemical process comprising at least two distillation columns. This definition is very broad and includes, for example, the catalytic cracking process for gasolines, and the process for producing paraxylene or metaxylenes from so-called "aromatics complex" aromatic fractions".

The following description and the example that illustrates the present invention are given in the case of the aromatics complex, although it is understood of course that this is merely one case of application and in no way restricts the scope of the disclosed method.

The process according to the present invention may be defined in general as a method for recovering low temperature heat in order to produce low pressure steam which, after recompression, can be used for various purposes, including heating the reboilers of some columns of the process in question, possibly after lowering the operating pressure of the said columns, so as to enable the reboiler of the said columns to operate at lower temperatures.

The method for recovering low temperature heat according to the present invention consists essentially in generating steam from the low-temperature heat available in the aromatics complex.

In practice, these heat sources are formed by the cooling towers of the overhead vapours of some columns, and the generation of LP steam is effected by replacing the cooling towers by exchangers termed LP steam vaporiser or generator.

The steam thereby generated thus has a temperature normally between 100° C. and 170° C.

This LP steam having a temperature between 100° C. and 170° C. can be used in various ways:

a) either this steam can be conveyed directly as heat transporting fluid in order to be used at different points of the aromatics complex, in particular (and in a non-limiting way) in the reboilers of some columns. This use corresponds to the circuit of the flow f1 of FIG. 2.

b) or it may be conveyed in a compression circuit comprising one or more compression stages generating medium pressure (MP) steam enabling one or more superheated fluids to be produced. These superheated fluids are then condensed, releasing their heat of condensation at various sites of the aromatics complex, in particular at the reboilers of some columns where the operating pressure has possibly been reduced. In order to obtain a sufficiently efficient heat exchange, it is recognised that the temperature of the hot fluids should preferably be between 5° C. and 15° C. above the temperature of the zones where the heat transfer takes place. This use corresponds to the circuit of the flow f3 of FIG. 2.

c) or this LP steam may be introduced into an expander so as to generate electricity. In this case turbo-expanders are preferably used, allowing a condensation of the steam below atmospheric pressure (abbreviated as "vacuum turbo-expander"). This use corresponds to the circuit of the flow f2 of FIG. 2.

The LP steams resulting from the uses a), b) or c) exist in the condensed state, and the resulting fluid may be treated in a condensate network so as to form a fluid capable of being recycled to the inlet of the various vaporisers in such a way as to form a closed water/steam loop (with a supply of demineralised water).

A closed utilities circuit is thus constructed, based on
the generation of low pressure steam in the condenser of a first series of distillation columns,
the use of this steam (compressed or not) as heat transporting agent for some cold fluids of the process, in particular the reboilers of a second series of distillation columns, or as a motive fluid for generating electricity, and then,
the recovery of the condensates after treatment so as to reconstitute the fluid intended for the vaporisations.

DETAILED DESCRIPTION OF THE FIGURES

Figure 1:
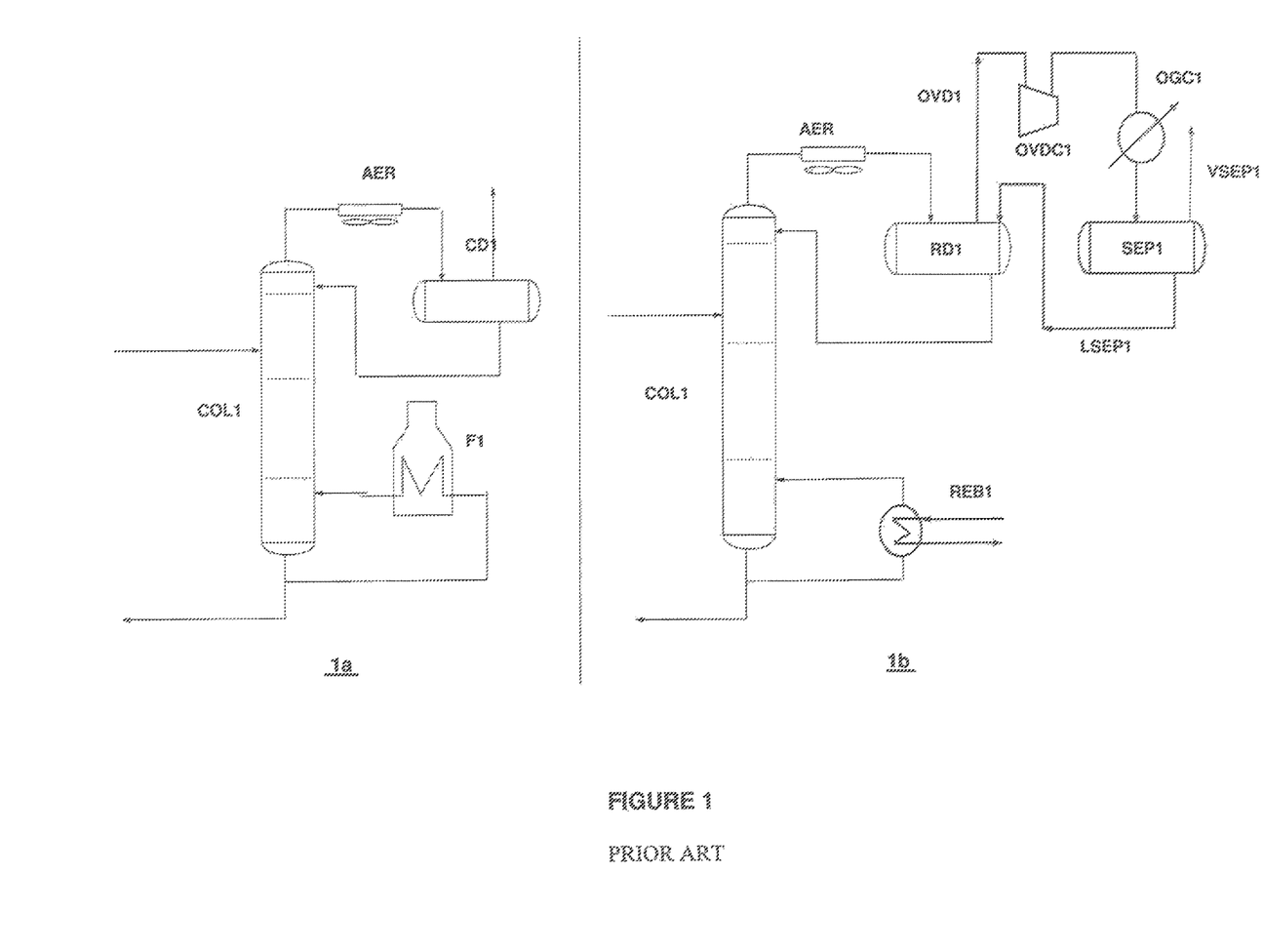
FIG. 1a is a flow scheme according to the prior art, which shows the basic configuration of a distillation column equipped with its overhead condenser and its bottom reboiler, the said reboiler being a furnace.
FIG. 1b according to the invention shows how it is possible to reduce the operating pressure of a distillation column by a system for compressing and cooling the overhead vapours from the said column. This modification of the operating pressure enables the temperature of the hot fluid required to reboil this column, and thus the amount of heat required to effect this reboiling, to be lowered.

FIG. 1a shows a column (COL1) according to the prior art provided with a reflux flask (CD1) that makes use of a cooling tower (AER) that cools the overhead flow from the column, and a reboiler, which is a furnace (F1).

The pressure of this column is minimised so as to be able to condense the vapours at a temperature at least greater than that of the available cold utilities, while limiting the losses of product through the degassed fluid at the head of the column. In order to stabilise effluents from the reaction section containing mixtures of substances having widely differing volatilities, this means operating the columns under a pressure of the order of 5 to 12 bars absolute.

FIG. 1b shows the modifications that have to be made at the head of the column (COL1) in order to compensate for the drop in operating pressure of the said column, and recover the gaseous phase supplement resulting from the said drop in pressure. At the bottom of the column the furnace has been replaced by a heat exchanger operating at a lower temperature.

More specifically, the system for condensing the overhead vapours from the column (COL1) modified according to the present invention may be described as follows: The overhead vapours from the column (COL1) are partially condensed, for example in a cooling tower (AER) and recovered in the form of a mixed phase in the reflux flask (RD1) of the column. The gas OVD1 that escapes from the reflux flask (RD1) is passed to the intake of the overhead gas compressor (OVDC1).

The gas at the outlet of the compressor (OVDC1) is partially (or completely) condensed via the condenser (OGC1). The flow leaving the condenser (OGC1) is recovered and separated in the flask (SEP1).

The liquid (LSEP1) from the flask (SEP1) is resent to the reflux flask (RD1) and the gas VSEP1 obtained from the flask (SEP1) is sent to another part of the unit or to the end of the unit.

Figure 2:
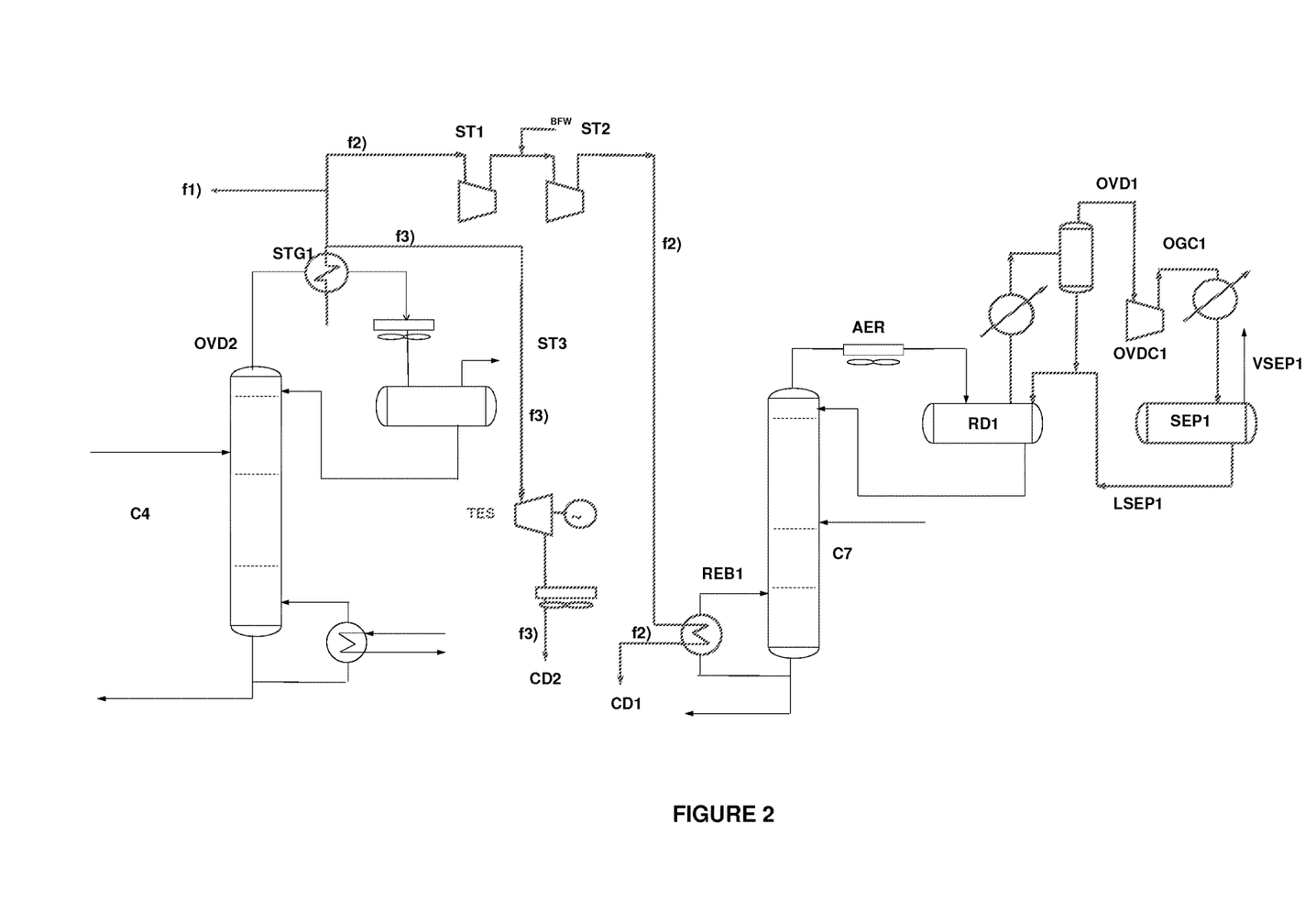
FIG. 2 according to the invention illustrates the generation of low-pressure and medium-pressure steam from the overhead condenser of the column denoted C4, and the use of medium pressure steam as heat transporting fluid for the reboiler of the column denoted C7.

FIG. 2 illustrates the uses corresponding to the circuits of the flows f2) and f3) of the LP steam obtained from the condensation of the overhead vapours from a column. The heat of condensation of the overhead vapours (OVD2) from the column C4 enables a liquid fluid to be vaporised via the heat exchanger (STG1). The pressure of this liquid is chosen so that its vaporisation temperature is less than that of the vapours OCD2 to be condensed.

The low pressure steam thus obtained is divided into three flows f1), f2) and f3) that follow different circuits, which may be described in the following way:
flow f1): a part of the LP steam may be passed directly as heat transporting fluid to the reboiler of some columns. This use of LP steam, which is very conventional for the person skilled in the art, is not illustrated in FIG. 2.
flow f2): another part of the LP steam is passed to two compression stages (ST1 and ST2) so as to generate the medium pressure steam that is used as heat transporting fluid in the reboiler (REB1) of the column C7. The steam is condensed (CD1) downstream of the reboiler (REB1). This use is in accordance with the present invention.
flow f3): another part of the LP steam is introduced into a LP steam turbine (TES) so as to generate electricity. At the outlet of the steam turbine (TES) the fluid is completely condensed in a cooling tower in order to produce a condensate (CD2).

This use is also according to the invention.

Figure 3:
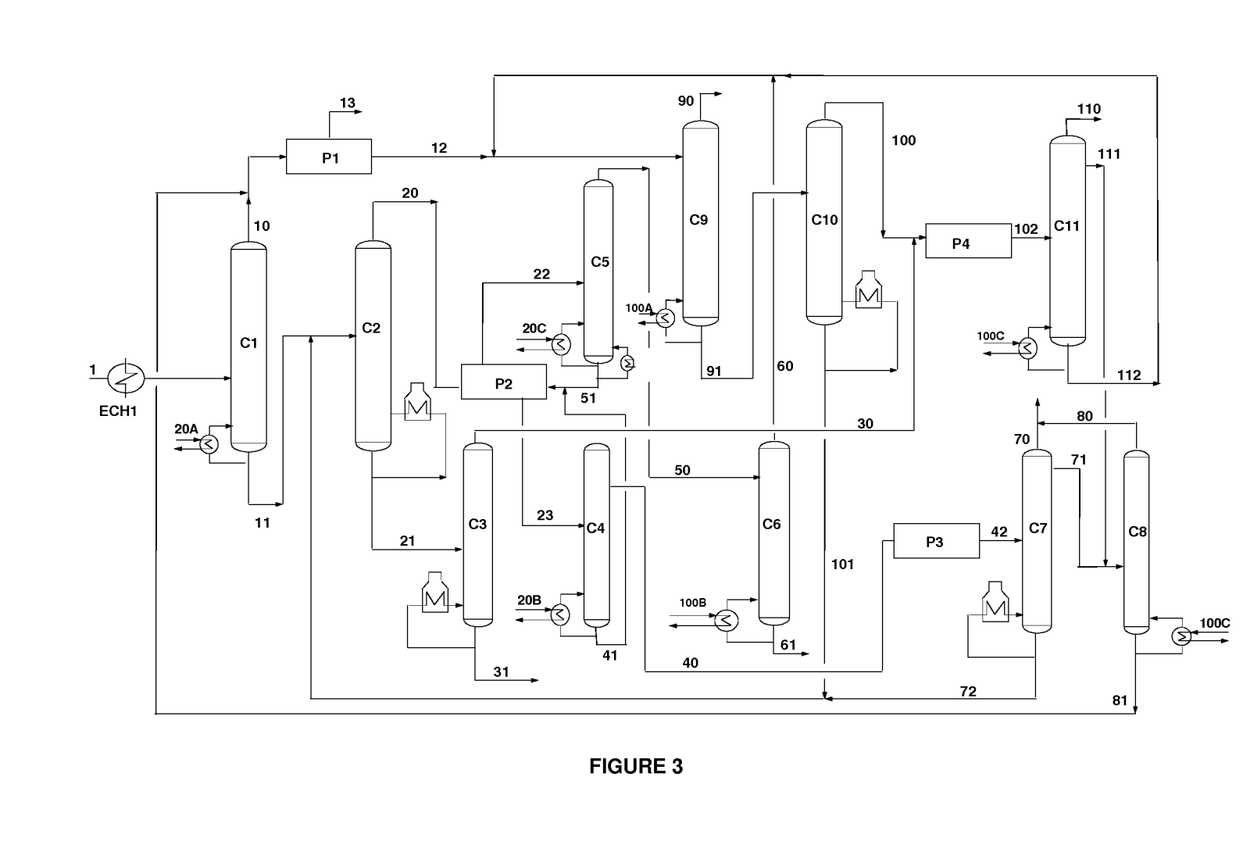
FIG. 3 is a process scheme of an aromatics complex according to the prior art.

FIG. 3 shows a typical process flow scheme of an aromatics complex according to the prior art, and is described in detail in the following paragraph.

Figure 4:
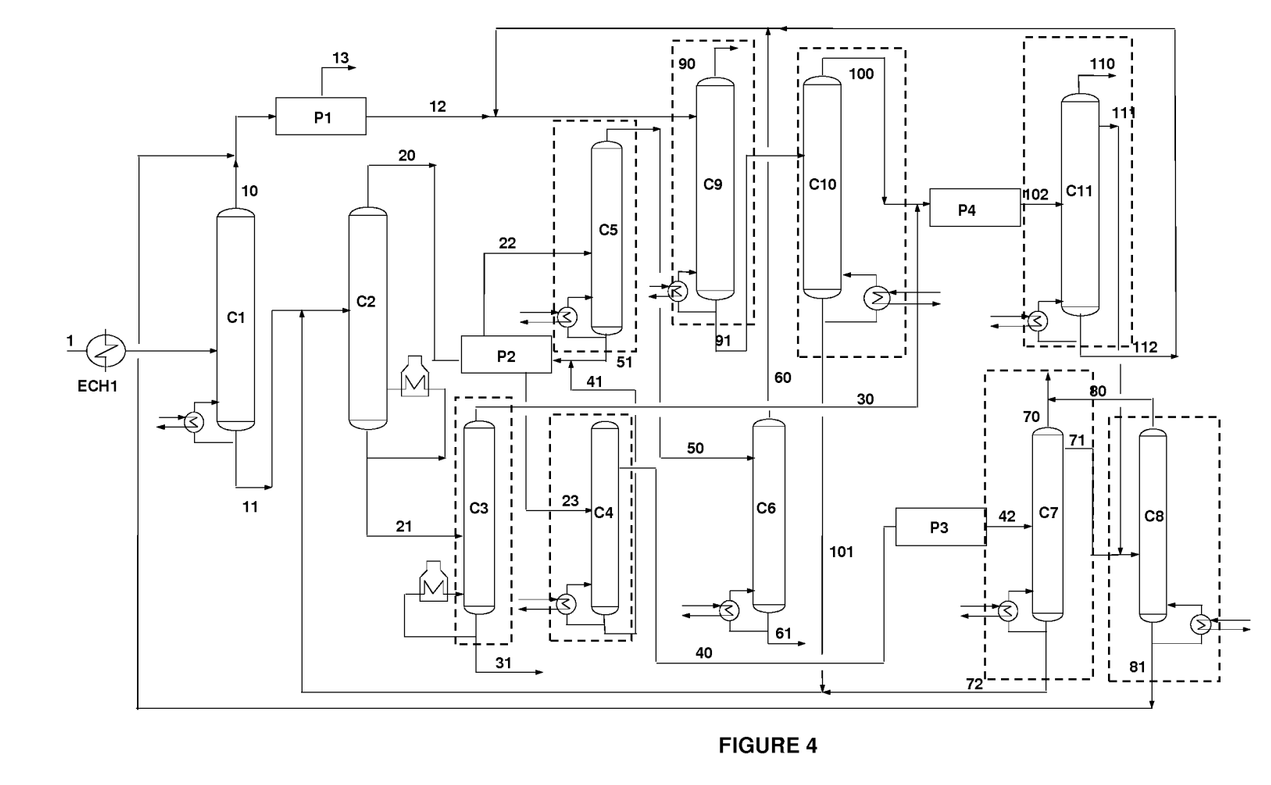
FIG. 4 is a process scheme of an aromatics complex according to the invention, i.e. including several low pressure steam circuits (outlined in bold lines) that relate to a certain number of columns.

FIG. 4 emphasises the zones of the aromatics complex that are modified according to the present invention compared to the typical process of the prior art (FIG. 3), by enclosing the said zones in dotted lines.

For the sake of simplicity the reflux sections, reflux flasks or condenser sections are not shown in FIGS. 2 and 4.
Example:

The following example is an application of the aforedescribed method in the case of an aromatics complex. A good understanding of this application requires a description of the aromatics complex per se, which is given with respect to FIG. 3 according to the prior art.

FIG. 4 according to the invention shows the zones of the aromatics complex that have been modified according to the means of the present invention:
reduction of the operating pressure of some columns of the complex,
utilisation of the overhead effluents of some columns in order to generate steam,
utilisation of the steam produced within the aromatics complex.

An aromatics complex such as described in the following example may be defined as a series of conversion and separation stages intended to produce aromatic compounds with eight carbon atoms, called xylenes, and more particularly paraxylene denoted PX, starting from a feedstock rich in aromatic compounds ranging from benzene to aromatic compounds with more than ten carbon atoms (denoted C10+) derived from a catalytic reforming unit. The feedstock should have very low to zero contents of sulphur and nitrogen compounds and olefins, since these compounds can affect the performances and the service life of some catalysts and molecular sieves employed in the units of the complex.

Reformate Column (C1)

The feedstock to be treated is conveyed via the line (1) and the exchanger ECH1 to a first distillation column denoted (C1), which separates the toluene and the lighter compounds from the heavier compounds (ranging from C8 to C10+).

The configuration of the reboiler and condenser of this column according to the prior art are shown in Table 1 below.

Extractive Distillation Unit (P1)

The toluene and the lighter compounds recovered at the head of the column C1 are passed via the line 10 to an extractive distillation unit denoted (P1), which separates a purely aromatic C6-C7 fraction from a product called "raffinate" consisting of paraffin compounds. The said raffinate is discharged from the complex via the line (13). The solvent that is preferably used in this extractive distillation unit is N-formylmorpholine (NFM).

Xylenes Column (C2)

C8-C10+ aromatic compounds recovered at the bottom of the column (C1) are passed via the line (11) to the so-called xylenes column (C2), which separates the C9 and heavier compounds from the C8 aromatic compounds (called xylenes), which supply the units of the complex situated downstream.

According to the prior art, the heat recovered by condensation of the overhead vapours from the column C2 is used to supply the necessary heat to the reboilers of the column C1, the column C4 (so-called raffinate column) and the column C5 (so-called extract column), which will be discussed hereinafter.

To this end, the operating pressure at the head of the column C2 is generally maintained at the required minimum pressure (generally between 7.0 and 9.0 bars absolute), which allows a condensation temperature of the overhead vapours from the xylenes column (C2) that is sufficient to be used as heat transporting fluid for the reboilers of the columns (C1), (C4) and (C5).

The configuration of the reboiler and condenser of this column according to the prior art are shown in Table 1 below.

Paraxylene Adsorption Unit (P2)

The xylenes fraction, i.e. a C8 aromatics fraction containing paraxylene, metaxylene and orthoxylene and ethylbenzene, is thus recovered at the head of the column C2 and is passed via the line (20) to the adsorption unit P2, which selectively recovers the paraxylene contained in the said fraction. The adsorption unit P2 thus produces a mixture of paraxylene and desorbent (called the extract), and a mixture of other C8 aromatic compounds and desorbent (called the raffinate).

The adsorbent is a molecular sieve specially intended for the adsorption of paraxylene, i.e. it has a particularly high affinity for this compound.

A commonly used solid adsorbent is a moulded faujasite-type zeolite with a silica binder exchanged with barium or potassium. The desorbent that is preferably used is paradiethylbenzene (PDEB).

Extraction Column (C5)

The flow of extract leaving the adsorption column and containing paraxylene and desorbent is passed via the line (22) to the extract column (C5), which separates the paraxylene from the desorbent.

The desorbent recovered at the bottom of the column (C5) is returned to the adsorption column via the line 51.

The extract column is preferably operated at low pressure, i.e. in a pressure range from 1.0 to 2.0 bars absolute in the reflux flask, so as to minimise the temperature of the reboiler and also the amount of heat to be supplied to the said reboiler.

According to the prior art the condensation of the overhead vapours from the extract column (C5) is performed by means of a cooling tower. The configuration of the reboiler and condenser of this column according to the prior art are shown in Table 1.

Purification Column (C6)

The flow from the head of the column (C5) is passed via the line (50) to the purification column (C6), which separates the toluene (which has been partially extracted with paraxylene) from the paraxylene. The toluene leaving the head of the column (C6) is passed via the line (60) to the inlet of the benzene column (C9). The high purity paraxylene that is produced is recovered at the bottom of the purification column (C6) and passed as finished product by pumping to the storage facility via the line (61).

Preferably the purification column C6 is operated at low pressure (in a pressure range from 1.0 to 2.0 bars absolute in the reflux flask), so as to minimise the temperature of the reboiler and the amount of heat to be supplied to the said reboiler.

The configuration of the reboiler and condenser of this column according to the prior art are shown in Table 1.

Raffinate Column (C4)

The raffinate flow obtained from the adsorption column (P2) is conveyed via the line 23 to the raffinate column (C4), which separates the C8 aromatics (raffinate) from the desorbent. The desorbent recovered at the bottom of the column (C4) is returned to the adsorption section (P2) via the line (41).

The raffinate (C8 aromatics fraction) is extracted as a side stream and passed via the line (40) as feedstock for the xylenes isomerisation unit (P3).

Preferably the column (C4) is operated at low pressure (in a pressure range from 1.0 to 2.0 bars absolute in the reflux flask) so as to minimise the temperature of the reboiler and also the heat to be supplied to the said reboiler. According to the prior art the condensation of the overhead vapours from the raffinate column (C4) is performed by means of a cooling tower.

The configuration of the reboiler and condenser of this column according to the prior art are shown in Table 1.

Desorbent Column (Not Shown in FIG. 3 or 4)

A small portion of the desorbent circulating in the adsorption section (P2) is passed to the so-called desorbent column so as to remove the heavy compounds that would otherwise accumulate in the loop.

The configuration of the reboiler and condenser of this column according to the prior art are shown in Table 1.

Xylenes Isomerisation Unit (P3)

The xylenes isomerisation unit (P3) is used to convert a feedstock depleted in paraxylene into a flow of xylenes at thermodynamic equilibrium.

Any type of catalyst capable of isomerising hydrocarbons with 8 carbon atoms can be used in the present invention. Preferably a catalyst is used that contains a dehydrogenating metal such as platinum, palladium or nickel and an acidic phase, for example a doped alumina, a zeolite such as mordenite, MFI, Y zeolite, or zeolitic or non-zeolitic molecular sieves exhibiting an acidity, such as aluminophosphates (AlPO, SAPO). More preferably there may therefore be used an isomerisation catalyst containing a EUO structural type zeolite, such as the zeolite EU1, the zeolite ZSM 50 or the zeolite TPZ3, as described in the patents U.S. Pat. No. 4,640,829, EP-B-042226 or EP-B-051318.

Deheptaniser (C7) and Stripper (C8)

The effluent from the isomerisation reactor (section (P3)) is passed via the line 42 to the deheptaniser (C7), which separates the isomer (C8+aromatic compounds) from a light C7 fraction recovered at the head of the said deheptaniser column (C7). This C7 fraction is passed via the line (71) to the stripping column (C8) in order to separate the light compounds from the C7 fraction.

The thereby stabilised C7 fraction is recovered at the bottom of the stripping column (C8) in order to be recycled via the line (81) and combined with the distillate coming from the column (C1) before being passed to the extractive distillation unit (P1).

According to the prior art the partial condensation of the overhead vapours from the deheptaniser column (C7) is performed by using a cooling tower, if necessary followed by a water cooler.

The limiting parameter that determines the operating pressure of the deheptaniser (C7) is the amount of recoverable compounds (such as benzene) that is lost through the degassed product in the reflux flask. In order to minimise these losses, the operating pressure in the reflux flask of the deheptaniser (C7) is generally maintained in a pressure range between 5.0 and 8.0 bars absolute.

The resultant temperature at the bottom of the deheptaniser (C7) is generally between 230° C. and 250° C., which requires the use of a source of heat at a temperature above 250° C. Generally the calorific fluid that is used is either high pressure steam, a furnace, or a hot oil. The C8+ fraction consisting of xylenes and heavy compounds recovered at the bottom of the deheptaniser (C7) is recycled via the line (72) to the inlet of the xylenes column (C2).

The configuration of the reboiler and condenser of the columns (C7) and (C8) according to the prior art is shown in Table 1.

Heavy Aromatics Column (C3)

The flow of C9+ aromatic compounds recovered at the bottom of the xylenes column (C2) is passed via the line (21) to the heavy aromatics column (C3), which separates the C9 and C10 aromatic compounds from heavier compounds (such as naphthalene), which have a harmful effect on the transalkylation catalyst. The heavy aromatics column is generally operated at low pressure (i.e. in a pressure range between 1.0 and 2.0 bars absolute in the reflux flask) so as to minimise the temperature and also the amount of heat to be supplied to the reboiler of the said column.

The configuration of the reboiler and condenser of the column C3 according to the prior art is shown in Table 1.

Transalkylation Unit (P4)

The C9 and C10 aromatic compounds recovered at the head of the heavy aromatics column (C3) are passed via the line (30) in order to be mixed with the toluene obtained from the toluene column (C10) so as to feed the transalkylation unit (P4). This unit converts the toluene and the C9+ aromatic compounds obtained from the reformate and the isomerate of the unit (P3) into a mixture of xylenes and benzene via a reaction that that is limited by the thermodynamics.

All types of transalkylation catalysts can be used in the process according to the invention, for example catalysts based on mordenite or faujasite described in U.S. Pat. No. 3,437,710 or the catalysts based on MCM-22 or beta zeolites described in U.S. Pat. No. 5,030,787, or catalysts based on mordenite and MFI zeolites such as described in U.S. patent application 2012/0065446. These catalysts generally also include a metallic compound preferably chosen from the group consisting of rhenium, nickel, cobalt, molybdenum, tungsten, palladium and platinum.

Stabilisation Column (C11)

The effluent from the transalkylation unit (P4), which contains benzene, unconverted toluene and C8 and C9+ aromatics, is passed via the line (102) to the stabilisation column (C11), which separates the compounds lighter than benzene, from benzene and heavier aromatic compounds denoted by C7+.

The gas leaving the reflux flask of the stabilisation column (C11) is passed via the line (110) to the end of the aromatics complex.

An unpurified benzene fraction is removed as a side stream and passed via the line (111) to the stripping column (C8), which enables the light compounds of the said fraction to be separated.

According to the prior art the partial condensation of the overhead vapours from the stabilisation column C11 is performed by means of a cooling tower, if necessary followed by a water cooler.

The limiting parameter that determines the operating pressure of the stabilisation column (C11) is the amount of recoverable compounds (such as benzene) that is lost through the gas leaving the reflux flask.

In order to minimise these losses, the operating pressure in the reflux flask of the stabilisation column (C11) is generally maintained in a pressure range between 5.0 and 8.0 bars absolute in the reflux flask.

The resultant temperature in the reboiler is between 210° C. and 230° C., which requires the use of a heat source in order to raise the temperature of the reboiler to above 230° C. (and which generally consists either of high pressure vapour, a furnace, or alternatively a hot oil).

The configuration of the reboiler and condenser of this column according to the prior art is shown in Table 1.

Benzene Column (C9)

The benzene is extracted from the head of the benzene column (C9) as final product via the line (90). The C7+ fraction is extracted at the bottom of the column (C9) and passed via the line (91) to the toluene column (C10).

The column (C9) is preferably operated at low pressure in a range from 1.0 to 2.0 bars absolute in the reflux flask so as to minimise the temperature as well as the amount of heat to be added to the reboiler.

The configuration of the reboiler and condenser of this column according to the prior art is shown in Table 1.

Toluene Column (C10)

The toluene recovered at the head of the toluene column (C10) is passed via the line (100) as feedstock for the transalkylation unit. The C8+ fraction extracted at the bottom of the column (C10) is recycled via the line (101) to the xylenes column (C2), which separates the C9+ and heavier compounds from the C8 aromatics fraction feeding the aromatics complex.

According to the prior art, a proportion of the heat of condensation of the overhead vapours from the toluene column (C10) is used to supply the necessary heat to the reboiler of the benzene column (C9).

To this end the operating pressure of the head tray of the toluene column (C10) is generally between 5.0 and 7.0 bars absolute, which allows a condensation temperature for the overhead vapours from the toluene column (C10) that is sufficient to be used for the re-boiling of the benzene column (C9).

The corresponding temperature at the bottom of the toluene column (C10) is between about 240° C. and 250° C., which requires a heat source to supply heat to the reboiler at a temperature above 250° C. (which generally consists either of high pressure steam, a furnace, or a hot oil).

The configuration of the reboiler and condenser of this column according to the prior art is shown in Table 1.

Table 1 according to the prior art summarises the means used for the condensation of the overhead vapours and the re-boiling of the bottom of the columns of the aromatics complex.

Table 2 according to the present invention shows the following features:

The set E1 of the columns that are used for the generation of low-pressure steam (in the example according to the invention columns C3, C4, C5) according to the principle of FIG. 2.

The set E2 of the columns that use the generated steam in order to supply heat to the reboiler (in the example according to the invention the columns C7, C8, C9, C10, C11).

In this set some columns function at a lower operating pressure: the columns (in the example according to the invention the columns C7, C8, C10, C11) and some (in the example according to the invention the columns C7 and C11) accordingly require a recompression stage for their overhead gas according to the flow diagram of FIG. 1b.

Some columns of the set E2 (in the example according to the invention the columns C7, C10, C11) use the MP steam obtained by two compression stages of the LP steam as heat transporting fluid for the re-boiling, according to the flow diagram of FIG. 2 (flow circuit f2).

Table 3 below summarises the energy gains of the aromatics complex according to the invention starting from a base 1 for the process according to the prior art. There is a noticeably significant gain as regards the three consumption items of fuel, steam production and electricity.

TABLE 1

Configuration of the reboilers and condensers of the columns according to the prior art

| | | Service | Condensation means overhead vapours | Re-boiling means |
|---|---|---|---|---|
| | | Fractionation of xylenes | | |
| | C1 | Reformate splitter | Cooling tower | Overhead vapour from xylenes column |
| | C2 | Xylenes column | Xylenes fraction - reboiler reformate splitter | Combustion furnace |
| | | | Adsorption of PX - reboiler extract column | |
| | | | Adsorption of PX - reboiler raffinate column | |
| | | | Extractive distillation of low temperature fraction - reboiler stripper | |
| | | Adsorption of paraxylene | | |
| | C5 | Extract column | Cooling tower | Overhead vapour from xylenes column |
| | C4 | Raffinate column | Cooling tower + water cooler | Overhead vapour from xylenes column |
| | | | | Hot oil circuit, bottom of xylenes column |
| | C6 | Purification column | Cooling tower | Feedstock of the adsorption section of PX |
| | | | | Desorbent of the adsorption section of PX |
| | | Desorbent column | (Not applicable) | Hot oil circuit bottom of xylenes column |
| | | Isomerisation of xylenes | | |
| | C7 | Deheptaniser | Feedstock of the deheptaniser | Combustion furnace |
| | | | Cooling tower | |
| | C8 | Stripper | (Not applicable) | MP steam reboiler |
| | | Transalkylation | | |
| | C3 | Heavy aromatics column | Cooling tower | Combustion furnace |
| | C11 | Stabilisation column | Cooling tower | Hot oil circuit, bottom of xylenes column |
| | | Benzene/Toluene fractionation | | |
| | C9 | Benzene column | Cooling tower | Overhead vapour of the toluene column |
| | C10 | Toluene column | Benzene column reboiler | Combustion furnace |
| | | | Cooling tower | |

TABLE 2

Application to an aromatics complex according to the invention

| Units | Service | Reduction in operating pressure | Overhead vapours used for steam generation | Use of the steam produced within the complex | Required number of steam compression stage |
|---|---|---|---|---|---|
| Fractionation of xylenes | | | | | |
| C1 | Reformate splitter | No | No | No | (n.a.) |
| C2 | Xylenes column | No | No | No | (n.a.) |
| Adsorption of paraxylene | | | | | |
| C5 | Extract column | No | Yes | No | (n.a.) |
| C4 | Raffinate column | No | Yes | No | (n.a.) |
| C6 | Purification column | No | No | No | (n.a.) |
| Isomerisation of xylenes | | | | | |
| C7 | Deheptaniser | Yes | No | Yes | 2 |
| C8 | Stripper | No | (n.a.) | Yes | 0 |
| Transalkylation | | | | | |
| C3 | Heavy aromatics column | No | Yes | No | (n.a.) |
| C11 | Stabilisation column | Yes | No | Yes | 2 |
| Benzene/Toluene Fractionation | | | | | |
| C9 | Benzene column | No | No | Yes | 1 |
| C10 | Toluene column | Yes | No | Yes | 2 |

Note
(n.a.) Not applicable
note 1:
(n.a.) denotes not applicable
note 2:
the pressure of the column C8 is reduced, since this pressure is adjusted to the pressure of the column C7.

TABLE 3

| | Prior art (FIG. 3) | Invention (FIG. 4) |
|---|---|---|
| Fuel consumption | 1.0 | 0.71 |
| Steam consumption | 1.0 | 0.84 |
| Electricity consumption | 1.0 | 0.58 |

The invention claimed is:

1. A method for recovering low-temperature heat between 100° C. and 180° C., from a low-temperature heat source in a refining or petrochemical process, called a "complex", comprising at least one distillation column, (P1), a unit of paraxylene adsorption (P2), xylenes isomerization unit (P3), and a transalkylation unit (P4), the effluents coming out from these units being separated in a set of distillation columns noted from C1 to C11, the signification of these columns being as follows:
   C1 reformate column, C2 xylenes column, C3 heavy aromatics column, C4 raffinate column, C5 extract column, C6 purification column, C7 deheptanisor, C8 striper, C9 benzene column, C10 toluene column, C11 stabilisation column, said method comprising the following stages:
   1) generating low pressure steam at a pressure between 1 bar absolute and 7 bars absolute by exchange with at least one low-temperature heat source that is a group of distillation columns C3, C4 and C5 of the complex, forming a first set of columns E1,
   2) increasing the pressure of the generated steam in at least one compression stage, in order to produce medium pressure steam,
   3) reducing the operating pressure of one or more distillation columns of the complex, so as to lower the temperature of a corresponding reboiler of that column below the temperature of the medium pressure steam obtained from stage 2,
   4) using at least a part of the low pressure steam obtained directly from stage 1 as heat transporting fluid supplied to the reboiler of column C9, and at least a part of the medium pressure steam obtained from stage 2, after compression, as heat transporting fluid supplied to the reboilers of columns C7, C8, C10 and C11 of the complex, said columns forming a second set of columns E2 distinct from E1.

2. The method for recovering heat according to claim 1, in which part of the low pressure steam obtained from stage 1 is used to generate electricity.

3. The method for recovering heat according to claim 1, in which stage 2 is carried out by means of a two-stage compressor.

4. The method for recovering heat according to claim 3, in which stage 2 is carried out by means of an ejector using high pressure steam as motive fluid.

5. The method for recovering heat according to claim 1, in which the low pressure steam obtained from stage 1, or the medium pressure steam obtained from stage 2, is used as heat transporting fluid in order to supply heat to combustion air of furnaces in air pre-heaters.

6. The heat recovery method according to claim 1, comprising recovering heat from an aromatics complex with at least one extractive distillation unit (P1), a paraxylene adsorption unit (P2), a xylenes isomerisation unit (P3) and a transalkylation unit (P4), the effluents from the said units being separated in distillation columns denoted C1-C11 with the following meanings:

C1 reformate column, C2 xylenes column, C3 heavy aromatics column, C4 raffinate column, C5 extract column, C6 purification column, C7 deheptaniser, C8 stripper, C9 benzene column, C10 toluene column, C11 stabilization column, in which:
- the low-temperature heat sources are distillation columns: C3, C4 or C5, which enable low pressure steam to be generated, said columns forming the set of columns E1,
- the columns to which the heat is supplied in the form of medium pressure steam after compression of low pressure steam generated by the set E1, or any sub-set thereof, and after reduction of operating pressure of the said columns C7, C8, C10, C11,
- the column to which the heat generated by the set E1, or a sub-set thereof, is supplied without pressure reduction to the column C9, the columns C7, C8, C9, C10 and C11 forming the set E2.

* * * * *